(12) United States Patent
Lee et al.

(10) Patent No.: US 8,008,272 B2
(45) Date of Patent: Aug. 30, 2011

(54) NUCLEASE-RESISTANT RNA APTAMER INHIBITING REPLICATION OF HEPATITIS C VIRUS REPLICON

(75) Inventors: Seong-Wook Lee, Seoul (KR); Kyung-Sook Shin, Seoul (KR); Jong-Hoon Lim, Seoul (KR)

(73) Assignees: Bexcore Co., Ltd., Seoul (KR); Daewon Pharm. Co., Ltd., Seoul (KR)

( * ) Notice: Subject to any disclaimer, the term of this patent is extended or adjusted under 35 U.S.C. 154(b) by 141 days.

(21) Appl. No.: 12/516,311

(22) PCT Filed: Jun. 8, 2007

(86) PCT No.: PCT/KR2007/002768
§ 371 (c)(1),
(2), (4) Date: May 26, 2009

(87) PCT Pub. No.: WO2008/066230
PCT Pub. Date: Jun. 5, 2008

(65) Prior Publication Data
US 2010/0160617 A1    Jun. 24, 2010

(30) Foreign Application Priority Data

Nov. 28, 2006  (KR) .................. 10-2006-0118062
Jun. 5, 2007   (KR) .................. 10-2007-0054744

(51) Int. Cl.
*C07H 21/02* (2006.01)
*C07H 21/04* (2006.01)
*A61K 31/70* (2006.01)
*C12Q 1/68* (2006.01)

(52) U.S. Cl. ............ 514/44 R; 514/44 A; 536/23.1; 536/24.3; 536/24.1; 536/24.5; 435/6

(58) Field of Classification Search ............ 435/6, 91.1, 435/91.31, 455; 514/44; 536/23.1, 24.5
See application file for complete search history.

(56) References Cited

U.S. PATENT DOCUMENTS

2005/0209180 A1   9/2005  Jadhav et al.
2006/0246421 A1  11/2006  Raney et al.

OTHER PUBLICATIONS

Shin, K-S et al., J. Microbiol. Biotechnol., vol. 16, No. 10, pp. 1634-1639 (2006).*
Shin Kyung-Sook et al., 'Inhibition of the Replication of Hepatitis C Virus Replicon with Nuclease-Resistant RNA Aptamers', In: *Journal of Microbiology and Biotechnology*, Oct. 28, 2006, vol. 16 (10), pp. 1634-1639.
Antonino Biroccio et al., 'Selection of RNA Aptamers That Are Specific and High-Affinity Ligands of the Hepatitis C Virus RNA-Dependent RNA Polymerase', In: *Journal of Virology*, Apr. 2002, vol. 76(8), pp. 3688-3696.
Hwang Byounghoon et al., 'Isolation of specific and high-affinity RNA aptamers against NS3 helicase domain of hepatitis C virus', In:*RNA*, Jul. 9, 2004, vol. 10(8), pp. 1277-1290.

* cited by examiner

*Primary Examiner* — Sean McGarry
(74) *Attorney, Agent, or Firm* — Lowe Hauptman Ham & Berner LLP

(57) ABSTRACT

Disclosed is a nuclease-resistant RNA aptamer for inhibiting the replication of HCV replicon. This aptamer is capable of binding specifically to HCV NS5B and inhibiting the proliferation of the HCV replicon, and includes at least one sequence selected from a group consisting of SEQ ID NOS. 1 to 4, in which a fluoro group is substituted for 2'-hydroxy of both U (uracil) and C (cytosine) bases, and SEQ ID NO. 17, in which the fluoro group is substituted for the 2'-hydroxy of both the U (uracil) and C (cytosine) bases, and which is tagged with a cholesteryl group at a 5' end and with idT at a 3' end. The RNA aptamer is useful in the diagnosis and treatment of HCV infection.

3 Claims, 9 Drawing Sheets

[FIG. 1]
RNA #9 (SEQ ID NO. 1)　　　RNA #24 (SEQ ID NO. 2)
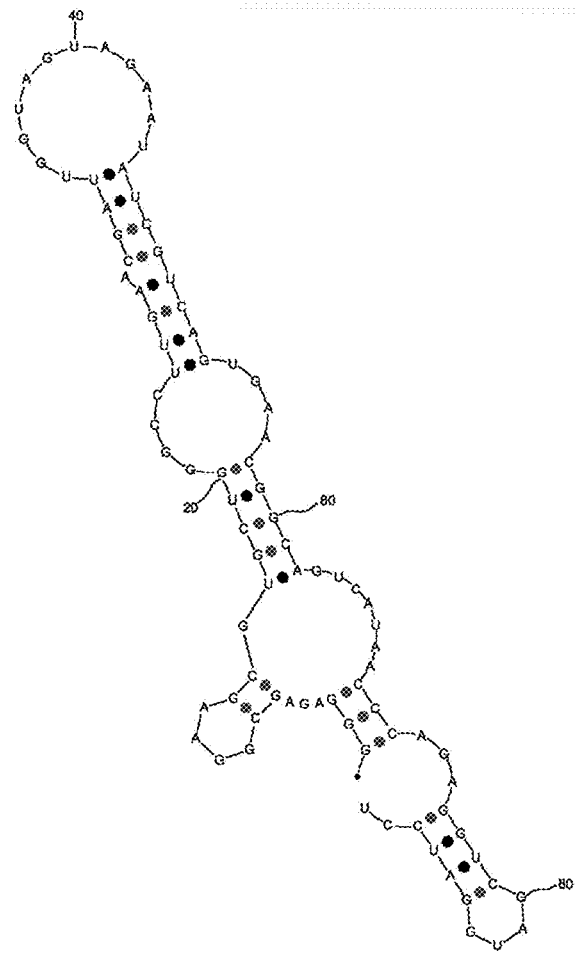
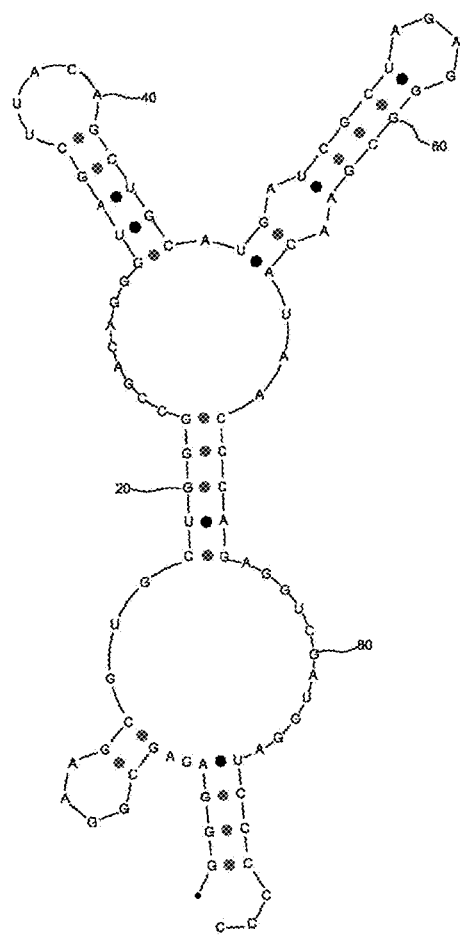
△G=−23.4 kcal/mole　　　△G=−32.3 kcal/mole

[FIG. 2]
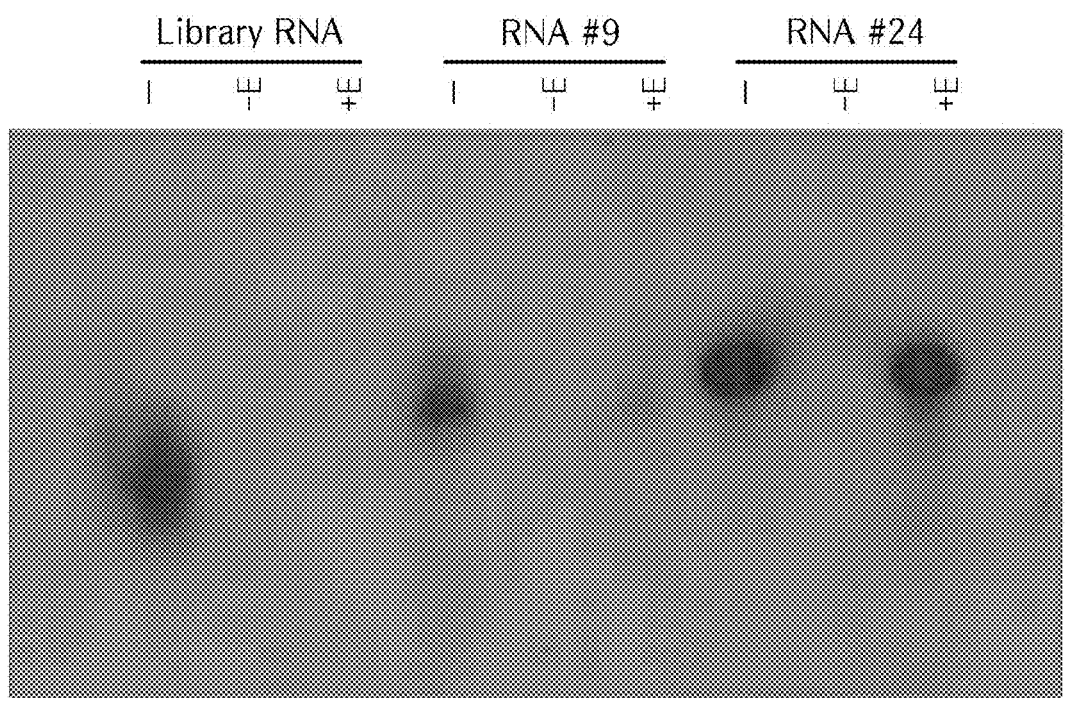

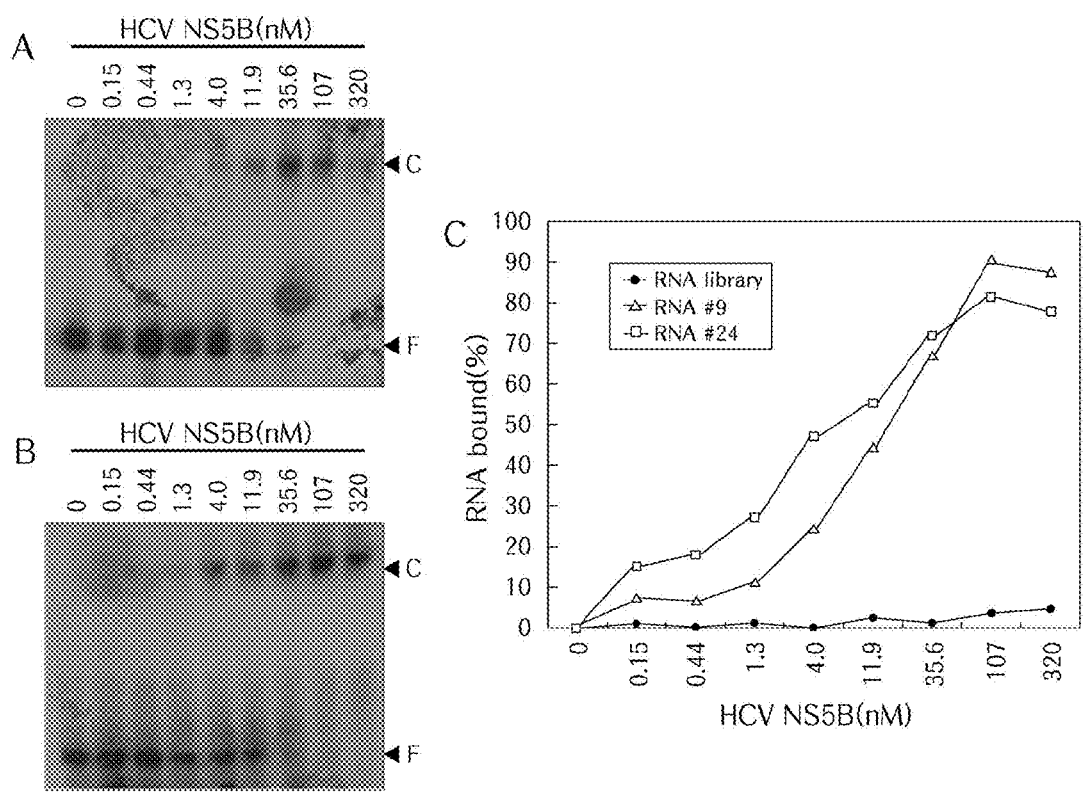
[FIG. 3]

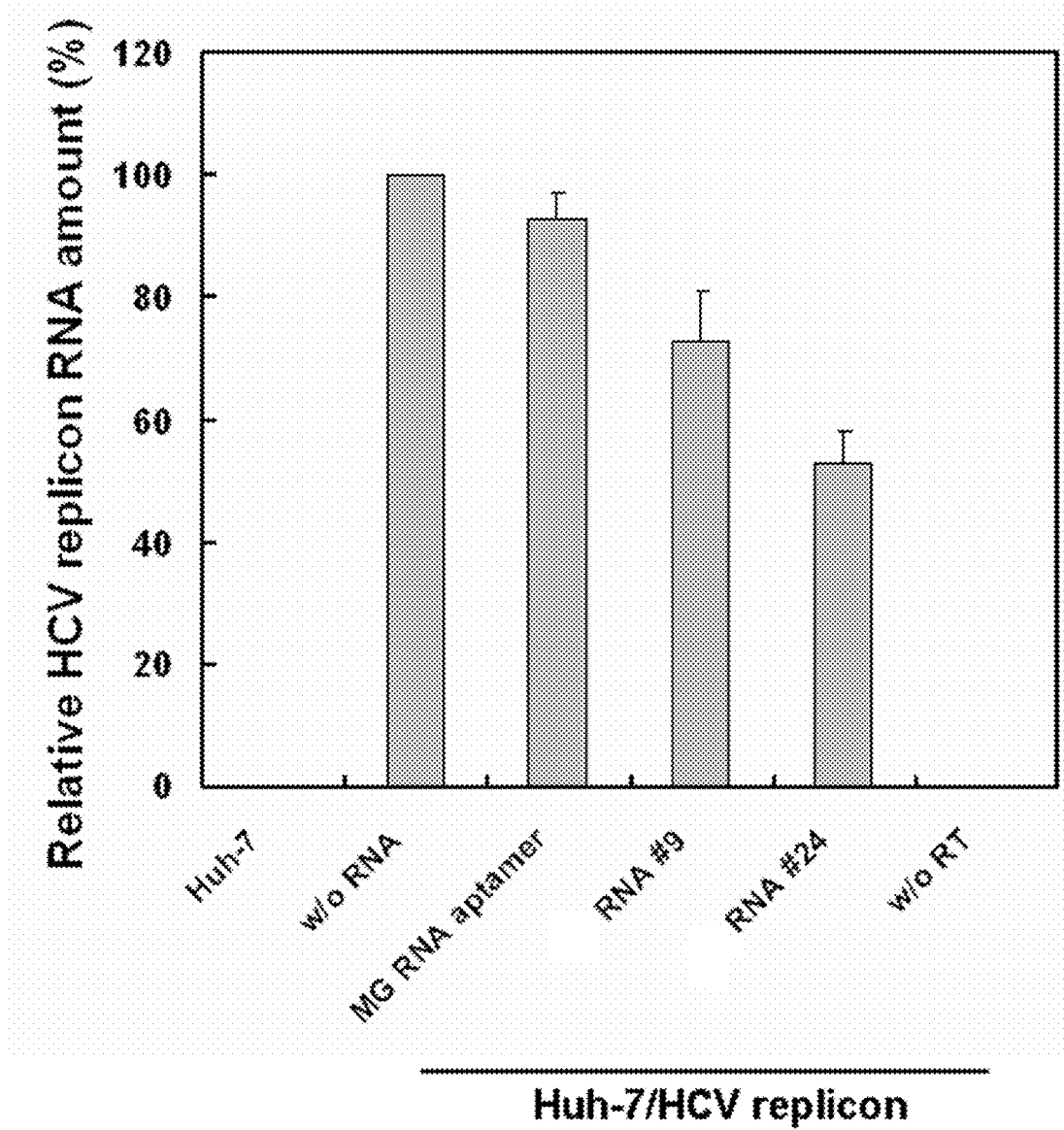
[FIG. 4]

[FIG. 5]
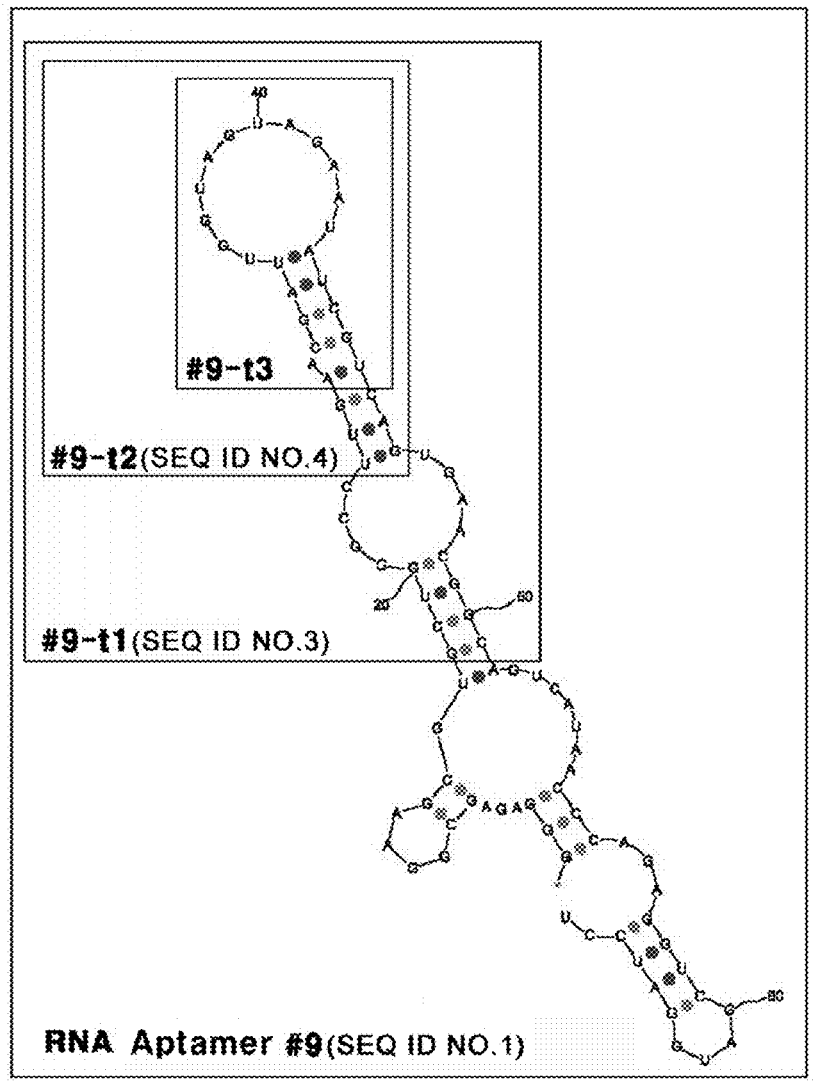

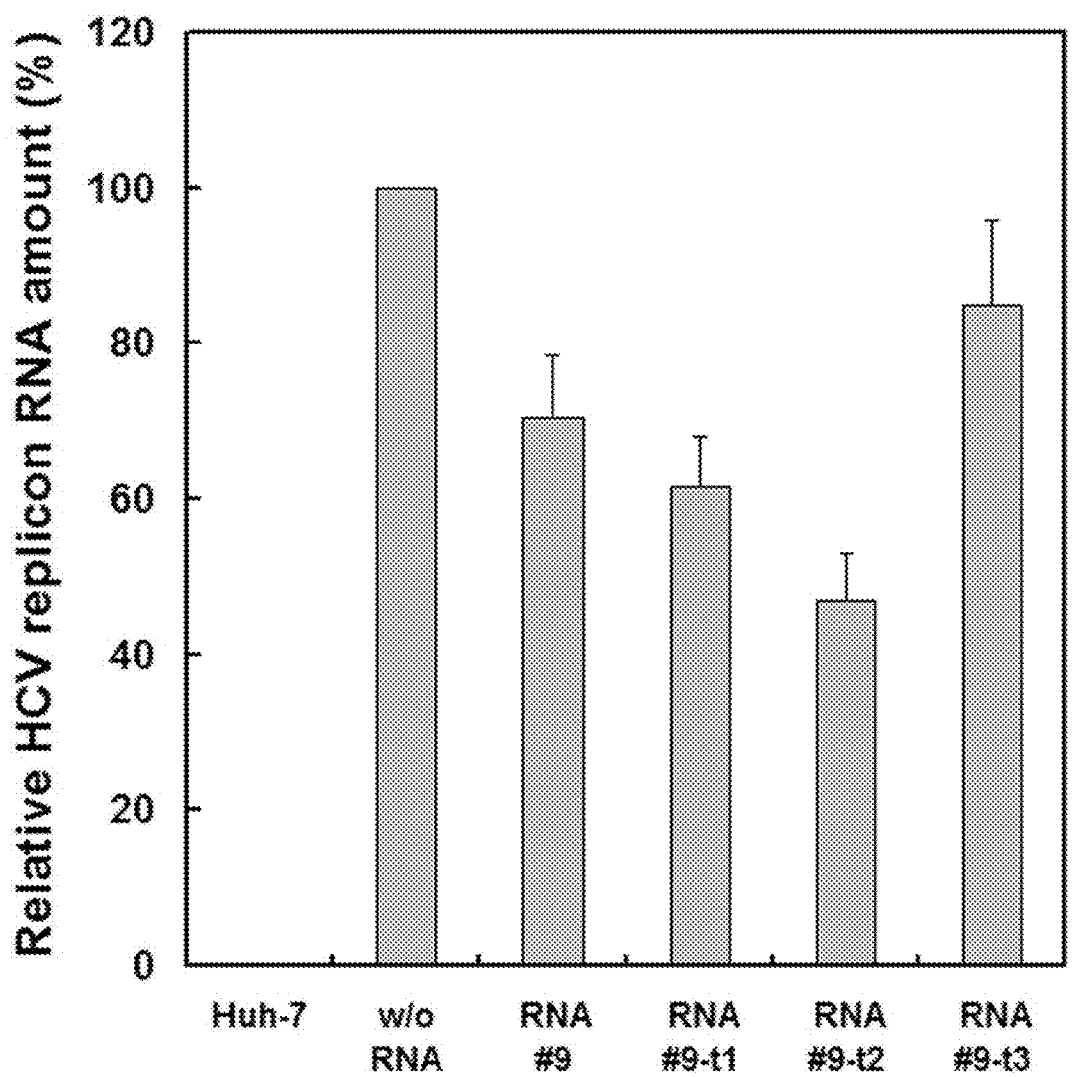
[FIG. 6]

[FIG. 7]
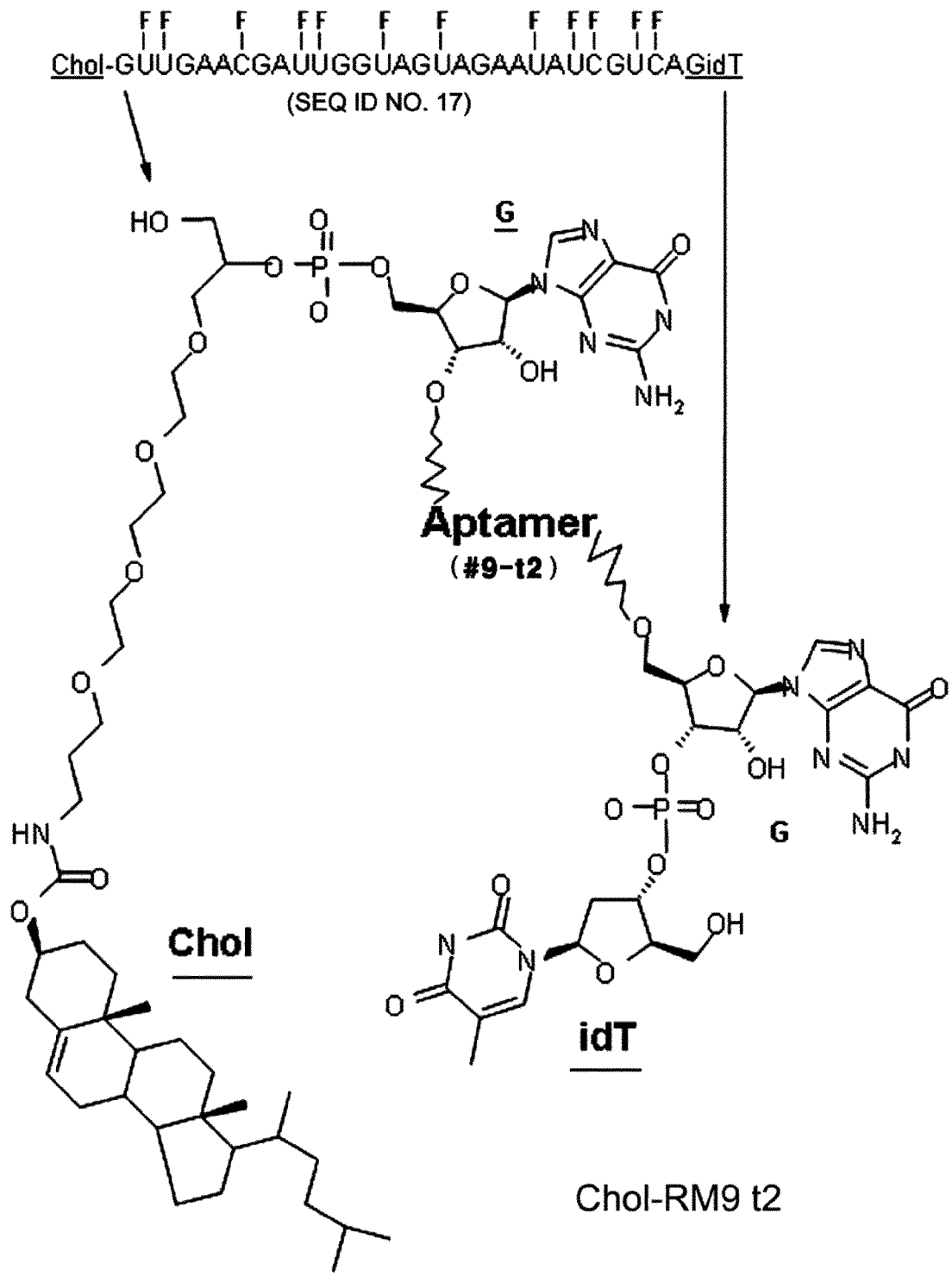

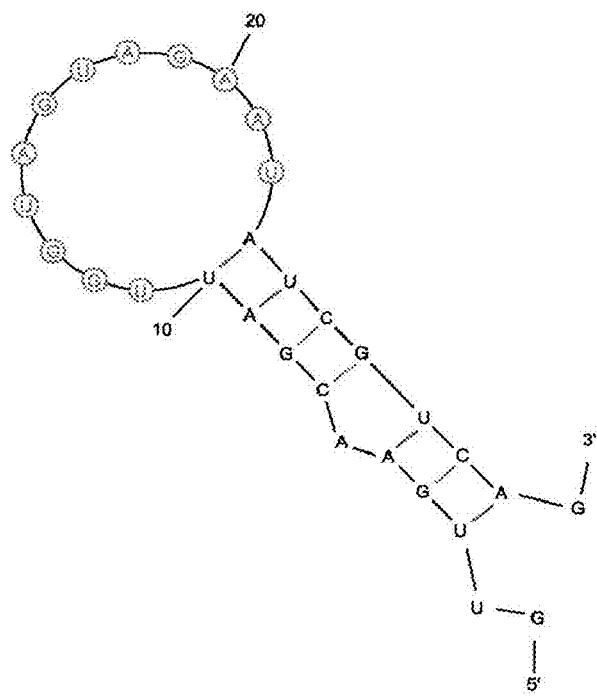
(Chol)-RM9 t2
(SEQ ID NO. 17)
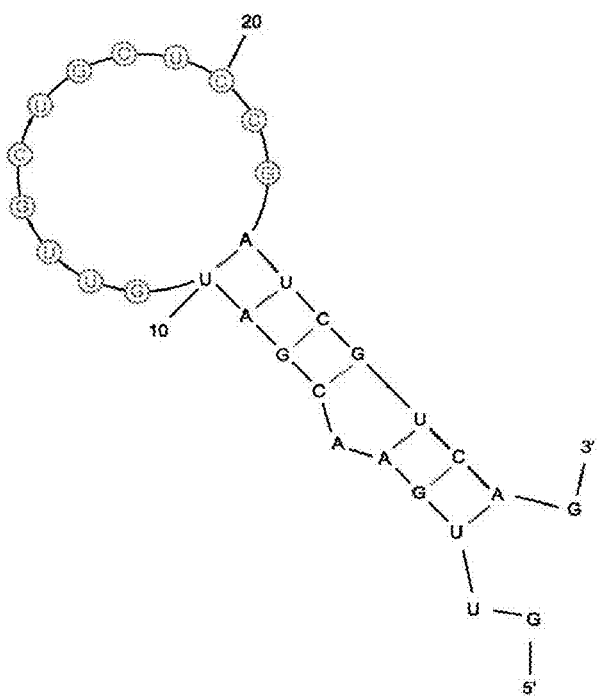
(Chol)-Mu-RM9 t2

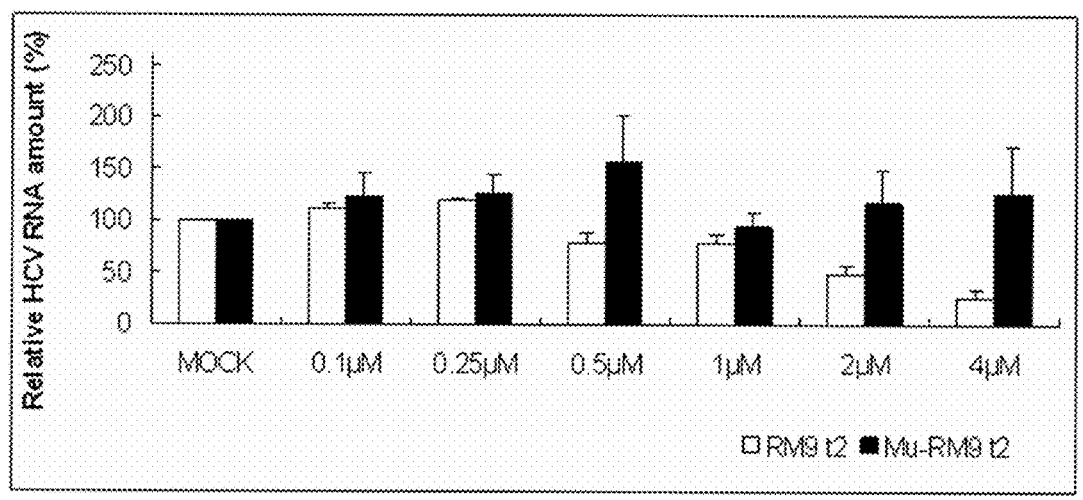
[FIG. 9]

SEQUENCE LISTING

```
<160> NUMBER OF SEQ ID NOS: 16

<210> SEQ ID NO 1
<211> LENGTH: 89
<212> TYPE: RNA
<213> ORGANISM: Artificial Sequence
<220> FEATURE:
<223> OTHER INFORMATION: Nuclease-resistant RNA aptamer specifically
      bound to the HCV NS5B and inhibiting replication of Hepatitis C
      virus replicon

<400> SEQUENCE: 1
gggagagcgg aagcgugcug ggccuugaac gauugguagu agaauaucgu cagugaacgg      60
cagucauaac ccagaggucg auggauccu                                        89

<210> SEQ ID NO 2
<211> LENGTH: 92
<212> TYPE: RNA
<213> ORGANISM: Artificial Sequence
<220> FEATURE:
<223> OTHER INFORMATION: Nuclease-resistant RNA aptamer specifically
      bound to the HCV NS5B and inhibiting replication of Hepatitis C
      virus replicon

<400> SEQUENCE: 2
gggagagcgg aagcgugcug ggccgacagg guagcuuaca gcugcaugau cgcuagaggg      60
cgaacauaac ccagaggucg auggaucccc cc                                    92

<210> SEQ ID NO 3
```

```
<211> LENGTH: 45
<212> TYPE: RNA
<213> ORGANISM: Artificial Sequence
<220> FEATURE:
<223> OTHER INFORMATION: Nuclease-resistant RNA aptamer specifically
      bound to the HCV NS5B and inhibiting replication of Hepatitis C
      virus replicon

<400> SEQUENCE: 3
gcugggccuu gaacgauugg uaguagaaua ucgucaguga acggc            45

<210> SEQ ID NO 4
<211> LENGTH: 29
<212> TYPE: RNA
<213> ORGANISM: Artificial Sequence
<220> FEATURE:
<223> OTHER INFORMATION: Nuclease-resistant RNA aptamer specifically
      bound to the HCV NS5B and inhibiting replication of Hepatitis C
      virus replicon

<400> SEQUENCE: 4
uugaacgauu gguaguagaa uaucgucag                              29

<210> SEQ ID NO 5
<211> LENGTH: 41
<212> TYPE: DNA
<213> ORGANISM: Artificial Sequence
<220> FEATURE:
<223> OTHER INFORMATION: Primer

<400> SEQUENCE: 5
ggtaatacga ctcactatag ggagagcgga agcgtgctgg g                41

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6 gggggatcc atcgacctct gggttatg                                28

<210> SEQ ID NO 7
<211> LENGTH: 44
<212> TYPE: DNA
<213> ORGANISM: Artificial Sequence
<220> FEATURE:
<223> OTHER INFORMATION: Primer

<400> SEQUENCE: 7
ggtaatacga ctcactatag ggctgggcct tgaacgaatg gtag             44

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
gccgttcact gacgatattc tactaccaat cgttcaagg                   39

<210> SEQ ID NO 9
<211> LENGTH: 36
<212> TYPE: DNA
<213> ORGANISM: Artificial Sequence
<220> FEATURE:
```

<223> OTHER INFORMATION: Primer

<400> SEQUENCE: 9
ggtaatacga ctcactatag ggttgaacga ttggta                          36

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
ctgacgatat tctactacca atcgttcaac cctata                          36

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
ggtaatacga ctcactatag ggaacgattg gta                             33

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
acgatattct actaccaatc gttccctata gtg                             33

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
ggggaattcc gtaacaccaa cgggcgc                                    27

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
gggaagcttc tcgtcctgca gttcat                                     26

<210> SEQ ID NO 15
<211> LENGTH: 32
<212> TYPE: DNA
<213> ORGANISM: Artificial Sequence
<220> FEATURE:
<223> OTHER INFORMATION: Primer

<400> SEQUENCE: 15
atctggcacc acaccttcta caatgagctg cg                              32

<210> SEQ ID NO 16

```
<211> LENGTH: 32
<212> TYPE: DNA
<213> ORGANISM: Artificial Sequence
<220> FEATURE:
<223> OTHER INFORMATION: Primer

<400> SEQUENCE: 16
cgtcatactc ctgcttgctg atccacatct gc                                      32
```

NUCLEASE-RESISTANT RNA APTAMER INHIBITING REPLICATION OF HEPATITIS C VIRUS REPLICON

CROSS REFERENCE TO RELATED APPLICATION

This application claims the priority of Korean Patent Application No. 10-2006-0118062, filed on Nov. 28, 2006, and Korean Patent Application No. 10-2007-0054744, filed on Jun. 5, 2007 in the KIPO (Korean Intellectual Property Office), the disclosure of which are incorporated herein in their entirety by reference. Further, this application is the National Phase application of International Application No. PCT/KR2007/002768, filed Jun. 8, 2007, which designates the United States and was published in English. Each of these applications is hereby incorporated by reference in their entirety into the present application.

TECHNICAL FIELD

The present invention relates to a nuclease-resistant RNA aptamer capable of inhibiting the replication of a hepatitis C virus replicon, and a kit for the diagnosis of hepatitis C virus infection and an inhibitor of hepatitis C virus replication using the same.

BACKGROUND ART

Hepatitis C virus (HCV) is the main pathogen causing chronic hepatitis, liver cirrhosis and, in some instances, hepatocellular carcinoma [refer to reference 14]. Although HCV affects more than 3% of the world population, no specific and efficient anti-HCV therapy has yet been developed.

HCV contains a single, positive-stranded RNA genome of about 9,600 nucleotides in length encoding a polyprotein of about 3010 amino acids [Reference 6]. This polyprotein precursor is co- or post-translationally processed into at least 10 mature structural and nonstructural proteins (C, E1, E2, p7, NS2, NS3, NS4A, NS4B, NS5A, and NS5B) by cellular and viral proteases [References 6 and 23].

HCV NS5B harbors RNA-dependent RNA polymerase activity [Reference 2], which is considered crucial for the synthesis of negative-strand and genomic viral RNA during HCV genome replication. Therefore, HCV NS5B is believed to be essential for viral proliferation, and hence, is a primary target for the development of antiviral drugs [Reference 18].

Characteristics of RNAs, in that they can adopt complex but stable structures to specifically and readily bind to target proteins, and can be chemically synthesized with ease, make RNAs potentially very useful diagnostic and/or therapeutic leading compounds [References 4 and 8].

Short RNA ligands, termed RNA aptamers, have been identified from a random RNA library to bind to a wide variety of proteins with high affinity and specificity using in vitro iterative selection techniques, called Systemic Evolution of Ligands by Exponential enrichment (SELEX) [References 7 and 28].

Several aptamers have been successfully evaluated in animal disease models [References 9, 24 and 26], and some of them are now in the therapeutic clinical development stage [Reference 27]. Of note, the U.S. FDA recently approved an RNA aptamer against anti-vascular endothelial growth factor (VEGF), called pegaptanib sodium (Macugen), for the treatment of all types of neovascular age-related macular degeneration [Reference 19], signifying tremendous therapeutic potential of RNA aptamers.

The isolation and characterization of high-affinity RNA aptamers specific for HCV NS5B has recently been achieved [References 3 and 29]. Although the isolated aptamers have been shown to inhibit the enzymatic activity of RNA-dependent RNA polymerase in vitro, no studies have described the inhibition of intracellular HCV replication with RNA aptamers against HCV NS5B.

Leading to the present invention, intensive and thorough research into inhibition against intracellular HCV replication, conducted by the present inventors, resulted in the finding that RNase-resistant RNA aptamers for HCV NS5B RNA-dependent RNA polymerase can inhibit HCV replication in human hepatoma cell lines.

DISCLOSURE OF INVENTION

It is an object of the present invention to provide an RNA aptamer capable of binding specifically to hepatitis C virus (HCV) NS5B.

It is another object of the present invention to provide an RNA aptamer for use in the treatment and diagnosis of hepatitis C infection, capable of binding specifically to HCV NS5B and inhibiting HCV replication.

It is a further object of the present invention to provide a kit for the diagnosis of HCV infection and an inhibitor of HCV, using an RNA aptamer capable of binding specifically to HCV NS5B and inhibiting HCV replication.

In accordance with an aspect thereof, the present invention provides a nuclease-resistant RNA aptamer capable of inhibiting the replication of the HCV replicon.

The RNA aptamer of the present invention consists of at least one sequence selected from a group consisting of SEQ ID NOS. 1 to 4, in which a fluoro group is substituted for 2'-hydroxy of both U (uracil) and C (cytosine) bases, and SEQ ID NO. 17, in which the fluoro group is substituted for the 2'-hydroxy of both the U (uracil) and the C (cytosine) bases, and which is tagged with a cholesteryl group at a 5' end and with idT at a 3' end.

Within liver cells, the nuclease-resistant RNA aptamer function to bind specifically to hepatitis C virus (HCV) NS5B and inhibit the proliferation of HCV replicon.

The sequences of SEQ ID NOS. 1 to 4 are as follows.

```
                                              (SEQ ID NO. 1)
5'-GGGAGAGCGGAAGCGUGCUGGGCCUUGAACGAUUGGUAGUAGAAUAU
CGUCAGUGAACGGCAGUCAUAACCCAGAGGUCGAUGGAUCCU-3'

(SEQ ID NO. 2)
5'-GGGAGAGCGGAAGCGUGCUGGGCCGACAGGGUAGCUUACAGCUGCAU
GAUCGCUAGAGGGCGAACAUAACCCAGAGGUCGAUGGAUCCCCCC-3'

(SEQ ID NO. 3)
5'-GCUGGGCCUUGAACGAUUGGUAGUAGAAUAUCGUCAGUGAACGG
C-3'

(SEQ ID NO. 4)
5'-UUGAACGAUUGGUAGUAGAAUAUCGUCAG-3'

(SEQ ID NO. 17)
5'-GUUGAACGAUUGGUAGUAGAAUAUCGUCAG-3'
```

In accordance with another aspect thereof, the present invention provides a kit for the diagnosis of HCV, comprising at least one RNA aptamer selected from a group consisting of SEQ ID NOS. 1 to 4, in which a fluoro group is substituted for 2'-hydroxy of both U (uracil) and C (cytosine) bases, and SEQ ID NO. 17, in which the fluoro group is substituted for the 2'-hydroxy of both the U (uracil) and the C (cytosine) bases, and which is tagged with a cholesteryl group at a 5' end and with idT at a 3' end, whereby the specific binding of the RNA aptamer to HCV NS5B can be detected.

In accordance with a further aspect thereof, the present invention provides an inhibitor of hepatitis C virus, capable of binding specifically to hepatitis C virus (HCV) NS5B and inhibiting the proliferation of the HCV replicon, comprising at least one RNA aptamer selected from a group consisting of SEQ ID NOS. 1 to 4, in which a fluoro group is substituted for 2'-hydroxy of both U (uracil) and C (cytosine) bases, and SEQ ID NO. 17, in which the fluoro group is substituted for the 2'-hydroxy of both the U (uracil) and the C (cytosine) bases, and which is tagged with a cholesteryl group at a 5' end and with idT at a 3' end.

As described above, HCV NS5B is an RNA-dependent RNA polymerase, a central catalytic enzyme in HCV replication, and thus is considered useful for use as a target molecule for exploiting anti-HCV agents.

From a combined RNA library comprising 40 random nucleotide sequences, in which a fluoro group is substituted for a hydroxy group at position 2' so as to confer nuclease resistance to the RNAs, nuclease-resistant RNA aptamers were developed using SELEX technology. The RNA aptamers of the present invention are identified as SEQ ID NO. 1 (RNA aptamer #9) and SEQ ID NO. 2 (RNA aptamer #24).

Whereas the library RNAs hardly bind to the target protein, the RNA aptamers of the present invention (SEQ ID NO. 1 and SEQ ID NO. 2) can bind specifically to HCV NS5B at high affinity, with Kd amounting to 18 nM and 5 nM respectively.

When introduced into the hepatoma cell line Huh-7, the RNA aptamers of the present invention were observed to suppress the RNA synthesis of the HCV subgenomic replicon and thus to inhibit HCV replication.

In the present invention, truncated constructs of the RNA aptamers of SEQ ID NO. 1 and SEQ ID NO. 2 were found to be optimized because they could strongly bind to HCV NS5B. The optimized RNA aptamers have SEQ ID NO. 3 (RNA aptamer #9-t1) and SEQ ID NO. 4 (RNA aptamer #9-t2).

The optimized RNA aptamer of SEQ ID NO. 4 (RNA aptamer #9-t2) in accordance with the present invention is only 29 nt in size and binds to NS5B at high affinity with Kd of 2.6 nM, inhibiting the RNA synthesis of HCV subgenomic replicon more effectively than the full-length RNA aptamer (SEQ ID NO. 1).

In the present invention, further, the optimized RNA aptamers are chemically synthesized. In this regard, the chemically synthesized RNA aptamers are tagged with a cholesteryl group at the 5' end for permeability to cells and with idT (inverted deoxy thymidylate) at the 3' end. When incubated with Huh-7 cells, these modified optimal RNA aptamers were observed to suppress the RNA synthesis of HCV subgenomic replicon in a dose-dependent manner more effectively compared to a mutant aptamer unable to bind to NS5B.

Therefore, the RNA aptamers of the present invention are expected to be useful in the diagnosis and treatment of HCV, and as tools for the study of RNA-dependent RNA polymerase.

As elucidated above, nuclease-resistant RNA aptamers against the HCV NS5B RNA-dependent RNA polymerase were identified with SELEX technology. These aptamers bind specifically and very readily to the target protein with a nanomolar binding constant. Importantly, the RNA aptamers can partially suppress intracellular RNA synthesis of the HCV replicon when introduced into human liver cells.

Recently, besides NS5B RNA replicase, several studies have been reported to isolate RNA aptamers against other HCV regulatory proteins such as NS3 helicase domain (References 10 and 11) or NS3 protease domain (Reference 13). However, such aptamers contained a normal 2'-hydroxyl group, and thus the aptamers must be expressed using their cDNA counterparts in order to inhibit HCV replication (Reference 20), which will entail large complications upon application to the development of anti-viral agents. By contrast, the obvious advantage of the nuclease-resistant RNA aptamers developed in the present invention is that the aptamers can be directly transferred into target cells, like small chemical compounds.

Notably, the aptamer (RNA aptamer #9-t2) of SEQ ID NO. 4, obtained from the RNA aptamers of the present invention through optimization, is only 29 nt in size, so that it can be readily chemically synthesized, and is expected to be very effective for practical use.

Further, the aptamer construct (Chol-RM9 t2; SEQ ID NO. 17), chemically modified from the optimized aptamer (SEQ ID NO. 4) with a cholesteryl group at the 5' end and idT at the 3' end, is resistant to nucleases and can pass through cell membranes. Thus, this aptamer of the present invention can effectively inhibit HCV replication when applied to cells.

Further modification of the aptamers, such as phosphothioate linkage or a terminal PEG (polyethyleneglycol) tag, will enhance the therapeutic potential thereof (Reference 5).

In addition to a therapeutic agent, the RNA aptamers could be used as diagnostic probes for HCV infection and as genetic tools to elucidate the intracellular role of the HCV NS5B during HCV multiplication.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows predicted structures of RNA aptamers according to the present invention, FIG. 2 shows the binding of an RNA aptamer according to the present invention to HCV NS5B, FIG. 3 shows high binding affinity of RNA aptamers according to the present invention to HCV NS5B replicase, FIG. 4 shows the inhibition of replication of the HCV replicon by RNA aptamers according to the present invention, FIG. 5 shows predicted structures of RNA aptamer #9 and its truncated constructs in accordance with the present invention, FIG. 6 shows the inhibition of replication of the HCV replicon by the optimized RNA aptamer according to the present invention, FIG. 7 shows a predicted structure of the chemically synthesized, optimized RNA aptamer, Chol-RM9 t2, in accordance with the present invention, FIG. 8 shows sequences and structures of the chemically synthesized aptamers, Chol-RM9 t2 RNA aptamer and Chol-Mu-RM9 t2 RNA aptamer, in accordance with the present invention, and FIG. 9 shows the inhibition of replication of the HCV replicon by the chemically synthesized aptamers, Chol-RM9 t2 RNA aptamer and Chol-Mu-RM9 t2 RNA aptamer, in accordance with the present invention.

BEST MODE FOR CARRYING OUT THE INVENTION

Below, a detailed description will be given of the present invention with reference to the accompanying drawings. First, the sequences of the RNA aptamers according to the present invention are determined and analyzed for characteristics, followed by the elucidation of the examples thereof.

1. Preparation of RNA Aptamers

For use in the preparation of an RNA library necessary for SELEX, a DNA library was constructed through PCR using the following 5'-primer (SEQ ID NO. 5) and 3'-primer (SEQ ID NO. 6), with 76-mer single oligonucleotides of 40 random bases serving as templates. The 5'-primer contained a T7 promoter region for RNA synthesis.

(SEQ ID NO. 5)
5'-GGTAATACGACTCACTATAGGGAGAGCGGAAGCGTGCTGGG-3'

(SEQ ID NO. 6)
5'-GGGGGGATCCATCGACCTCTGGGTTATG-3'

In this regard, a PCR solution was prepared to contain 0.25 µM 5'-primer, 0.25 µM 3'-primer, a 10×PCR buffer and 100 µM dNTP. After initial denaturation for 5 min at 95° C. in the presence of 2.5 units of Tag polymerase (Promega), PCR was performed for 30 cycles of 30 sec at 95° C., 30 sec at 55° C. and 1 min at 72° C., followed by elongation for 8 min 30 sec at 72° C. to give a DNA library.

An RNA library was prepared using T7 RNA polymerase (Takara) through the in vitro transcription of the DNA library prepared above. In this regard, a random pool of RNA oligonucleotides resistant to nuclease was generated, with every pyrimidine modified at its 2' position by a fluoro group by the in vitro transcription of synthetic DNA templates with 2'-deoxy-2'-fluoro CTP and UTP (Epicentre Technologies) and normal GTP, ATP, and T7 RNA polymerase (Reference 25).

In greater detail, 50 µl of a mixture of the DNA library, a 5× transcription buffer, 50 mM DTT, 0.5 mM ATP, GTP, 2'-F CTP, 2'-F UTP, T7 RNA polymerase (Takara), and DEPC—H$_2$O were reacted at 37° C. for 3 hrs. After the removal of the DNA templates by digestion with 5U RQ1 DNaseI (Promega) at 37° C. for 30 min, the RNA library was extracted using Sephadex (sigma). The RNA obtained through SELEX was extracted from 7M urea-6% polyacrylamide gel.

The sequence of the resulting RNA library was 5'-GG-GAGAGCGGAAGCGUGCUGGGCC N$_{40}$ CAUAACCCA-GAGGUCGAUGGAUCCCCCC-3', where N$_{40}$ represents 40 nucleotides (nts) with the equimolar incorporation of A, G, C, and U at each position.

A recombinant fragment of HCV NS5B RNA-dependent RNA polymerase was cloned into a pET21 expression vector (Novagen), which expresses recombinant proteins tagged with a hexahistidine at the C-terminus. Proteins were overexpressed in *E. coli* BL21 (DE3) strain and purified with nickel-chelate resin (Ni-NTA agarose) [Reference 22].

SELEX was performed to isolate RNase-resistant RNA aptamers specific to the HCV NS5B [References 1, 10 and 25], with a few modifications. First, 10 µg of the RNA library was preincubated with 20 µl of Ni-NTA agarose beads in 100 µl of binding buffer (30 mM Tris-HCl, pH 7.5, 150 mM NaCl, 1.5 mM MgCl$_2$, 2 mM dithiothreitol, and 1% BSA) for 30 min at room temperature with shaking. The RNA-bead complexes were then precipitated and discarded to remove any RNA that nonspecifically bound to agarose beads.

The precleared supernatant was transferred to a new tube and further incubated with His-tagged HCV NS5B for 30 min at room temperature. The NS5B-RNA complexes were precipitated with beads, and pellets were washed five times with 0.5 ml of the binding buffer.

The RNAs were recovered, amplified with RT-PCR and in vitro transcription, and used for 7 more rounds of selection. After 8 rounds of selection, the amplified DNA was cloned, and 14 clones were sequenced.

2. Binding Specificity of RNA Aptamers

The previously selected RNA aptamers were internally labeled with [alpha-32P] ATP. In this regard, RNA aptamers were generated from the cDNA clones using T7 RNA polymerase in the presence of [alpha-32P] ATP.

After being denatured at 95° C. for 2 min, the RNA fragments were separated in 7M urea-6% polyacrylamide gel by electrophoresis and then exposed to an X-ray film for 3 min. RNA bands of interest were excised with reference to the developed X-ray film, and eluted at 37° C. for 3 hrs with 400 µl of an elution buffer. The eluted RNA was isolated and concentrated through phenol extraction and ethanol precipitation, followed by quantitative analysis with a liquid scintillation counter.

Then, the RNA aptamers were assayed for binding specificity for HCV NS5B. To this end, 1 nM of the RNAs was incubated with 100 nM of NS5B for 30 min at room temperature in 100 µl of a binding buffer (30 mM Tris-HCl (pH 7.5), 150 mM NaCl, 1.5 mM MgCl$_2$, 2 mM DTT).

After being precipitated with Ni-NTA agarose beads, NS5B-RNA complexes were washed five times with 0.5 ml of a binding buffer. The bound RNAs were extracted from the pellets using 15 µl of 0.1M EDTA and phenol. The RNA concentrate obtained through ethanol precipitation was analyzed on 6% polyacrylamide gel with urea.

As a result, RNA aptamers of SEQ ID NO. 1 (RNA aptamer #9) and SEQ ID NO. 2 (RNA aptamer #24) in accordance with the present invention were prepared.

3. Construction of Truncated RNA. Aptamers

Truncated forms of the RNA aptamers of SEQ ID NO.: 1 (RNA aptamer #9) and SEQ ID NO. 2 (RNA aptamer #24) were constructed by in vitro transcription using T7 polymerase, as follows.

PCR was performed using 5'- and 3'-primers of respective SEQ ID NOS. 7 and 8 for the amplification of RNA aptamer #9-t1 (SEQ ID NO. 3), 3'-primers of respective SEQ ID NOS. 9 and 10 for the amplification of RNA aptamer #9-t2 (SEQ ID NO. 4), and 3'-primers of respective SEQ ID NOS. 11 and 12 for the amplification of RNA aptamer #9-t3 (SEQ ID NO. 3).

(SEQ ID NO. 7)
5'-GGTAATACGACTCACTATAGGGCTGGGCCTTGAACGAATGGTAG-3'

(SEQ ID NO. 8)
5'-GCCGTTCACTGACGATATTCTACTACCAATCGTTCAAGG-3'

(SEQ ID NO. 9)
5'-GGTAATACGACTCACTATAGGGTTGAACGATTGGTA-3'

(SEQ ID NO. 10)
5'-CTGACGATATTCTACTACCAATCGTTCAACCCTATA-3'

(SEQ ID NO. 11)
5'-GGTAATACGACTCACTATAGGGAACGATTGGTA-3'

(SEQ ID NO. 12)
5'-ACGATATTCTACTACCAATCGTTCCCTATAGTG-3'

RNAs were generated with every pyrimidine modified at its 2' position by a fluoro group by the in vitro transcription of the amplified double-stranded DNA using T7 RNA polymerase. The RNAs were separated on 10% denaturing urea gel by electrophoresis.

As a result, SEQ ID NO. 3 (RNA aptamer #9-t1) and SEQ ID NO. 4 (RNA aptamer #9-t2) were found to be ideal for use with the present invention.

4. Synthesis of RNA, Aptamer

The optimized RNA aptamer #9-t2 (containing 2'-fluoropyrimidine) in accordance with the present invention was synthesized using standard solid-phase phosphoramidite chemistry, and purified with HPLC (high speed liquid chromatography).

At this time, mutant aptamers which could not bind to NS5B were also synthesized. Both the optima and the mutant aptamers were tagged with idt (inverted dT) at the 3' end to protect themselves from nucleases, and with cholesterol at 5' end to pass through cell membranes.

The synthesis of the modified aptamers was conducted on a 1 mmol scale using idT CPG (solid support). For the attachment of cholesterol group to 5' end, cholesteryl TEG amidite (1-dimethoxytrityloxy-3-O—(N-cholesteryl-3-aminopropyl)-triethyleneglycol-glyceryl-2-O-(2-cyanoethyl)-(N,Ndi-isopropyl)-phosphoramidite) was used.

The aptamer conjugate with a cholesteryl group was identified by polyacrylamide gel electrophoresis, HPLC and 20 MALDI-TOF, isolated through precipitation and desalting processes using CentriSep (Princeton Separations Inc.), and dissolved in water before use in experiments. The final optimized aptamer and the mutant aptamer, chemically synthesized, were named Chol-RM9 t2 (SEQ ID NO. 17) and Chol-Mu-RM9 t2, respectively.

5. Assay for Binding Affinity of RNA Aptamer (1) Gel Retardation

An internally radiolabeled RNA aptamer (50 µM) was reacted with increasing amounts (0-320 nM) of NS5B. For this, the aptamer, the protein, a binding buffer (30 mM Tris-HCl (pH 7.5), 150 mM NaCl, 1.5 mM $MgCl_2$, 2 mM DTT), and 3 µg of tRNA were mixed to achieve a total volume of 40 µl before incubation at room temperature for 30 min. 6×BPB was added and electrophoresis was conducted on a 6% native gel (6% polyacrylamide, 1×TBE, 10 mM $MgCl_2$, 2% glycerol) at 4° C. in the presence of an electric field of 120 V. After the exposure of the gel to an X-ray film, it was developed. The proportion of NS5B-bound RNA aptamer to total RNA aptamer was measured to calculate the dissociation constant (Kd).

(2) SPR Analysis

The CM5 sensor chip of a Biacore 2000 instrument was activated by injecting 50 µl of a mixture of equal volumes of NHS and DEC at a flow rate of 5 s/min for 40 sec. When 150-200 RU appeared, a protein to be immobilized was diluted to a concentration of 50 ng/µg in sodium acetate (pH 4.0) before injection. Subsequently, 50 mM NaOH was injected for 5 sec to examine whether ligand immobilization was achieved accurately. The RNA aptamer was denatured at 80° C. for 5 min and renatured at room temperature for 15 min to prepare an RNA specimen as an analysis target. The flow rate was changed to 30 s/min in order to obtain the kinetics of the analysis targets. A dilution of the analysis target in 1×HBS was injected at a concentration between 6.25 nM and 500 nM. At each step, renaturation was conducted with 50 mM NaOH. After the equilibrium dissociation constant (Kd) between the ligand and the analysis target was set at 1:1 binding therebetween, KD values were obtained from the plot of Req values of a sensogram using a kinetic simultaneous Ka/Kd model program.

6. Inhibition of RNA Aptamer Against HCV Proliferation

The RNA aptamers were evaluated for ability to suppress HCV replication in human liver cells using recently developed HCV subgenomic replication systems (References 12 and 17).

A subgenomic replicon construct, pFK-$I_{389}$neo/NS3-3'/5.1 [Reference 12], carrying two cell culture adaptive mutations in NS3 and one in NS5A, was obtained from Dr. Ralf Bartenschlager in the University of Heidelberg, Germany. HCV replicon RNA was then constructed by in vitro transcription with the AseI and ScaI-digested replicon plasmid, as described [Reference 10].

To determine whether the selected RNA inhibited the intracellular HCV replication, the level of synthesized HCV negative (−) strand RNA in hepatocarcinoma Huh-7 cells was quantified by RT-PCR 72 hrs after cotransfection with the HCV replicon RNA and various RNA competitors.

An electroporation experiment was employed for RNA transfection into a suspension of $4 \times 10^6$ Huh-7 cells with 500 ng of the HCV replicon RNA along with 5 µg of tRNA under conditions of 950 µF and 250 V using a Gene Pulser system (BioRad). Plasmid pcDNAluc, encoding *Renilla* luciferase, was also added to each sample to assess transfection efficiency.

Similar transfection efficiency in each sample was confirmed through RT-PCR analysis of the luciferase gene.

After 72 hrs of transfection, total RNA was isolated and reverse-transcribed with a 3' primer specific for the negative strand of HCV cDNA (5'-GGGGAATTCCGTAACAC-CAACGGGCGC: SEQ ID NO. 13) or random primers for β-actin cDNA.

The resulting cDNAs were amplified for 30 cycles with a 5' primer (5'-GGGAAGCTTCTCGTCCTGCAGTTCAT: SEQ ID NO. 14) and a 3' primer specific for the HCV (−) strand cDNA. Values were normalized to those of β-actin, which were amplified with a 5'-primer (5'-ATCTGGCACCACAC-CTTCTACAATGAGCTGCG: SEQ ID NO. 15) and a 3'-primer (5'-CGTCATACTCCTGCTTGCTGATCCA-CATCTGC: SEQ ID NO. 16).

Huh-7 cells in which a subgenomic replicon construct, pFK-$I_{389}$neo/NS3-3'/5.1 RNA, was stably replicated were observed for the inhibition of the chemically synthesized aptamers against HCV subreplicon RNA replication.

Huh-7 cells in which the HCV subgenomic replicon was replicated were incubated at 37° C. with various concentrations of Chol-RM9 t2 and Chol-Mu-RM9 t2 aptamers. After 48 hrs of incubation, total RNA was isolated and subjected to real-time RT PCR to observe the extent to which the RNA replication of the HCV subgenomic replicon was inhibited. For real-time RT-PCR, an SYBR-Green core reagent kit was used in combination with Tag polymerase (Takara).

When sets of primers specific for the negative strand of HCV cDNA, described above, were used to amplify the negative strand, its amount in the cells transfected with the aptamers was compared with that in mock transfected cells.

The amplification of the negative strand of HCV cDNA was conducted with 2 mg of total RNA according to a PCR-kit manual [12.5 ml SYBR Green Mix (2×), 0.2 ml cDNA, 1 ml primer pair mix (5 pmol/ml each primer), and 11.3 ml H2O].

PCR was performed with 40 cycles of 95° C. for 30 sec, 55° C. for 40 sec and 72° C. for 1 min.

A GAPDH gene was used as a house keeping control gene for PCR products in order that the limit standard obtained with HCV cDNA was adjusted to that obtained with GAPDH to correct a minimal fluctuation in cDNA load. For amplification, Roter-Gene and a real-time PCR apparatus (Corbett) were employed.

Example 1

Selection of RNase-Resistant RNA Aptamers Specific for HCV NS5B

For the selection of RNA aptamers specific for HCV NS5B, a random pool of RNA oligonucleotides of about $10^{14}$ different molecules was generated, with every pyrimidine modified at its 2' position by a fluoro group. This modification of the 2' position of RNA increased its stability in human serum more than 10,000 fold compared with unmodified 2'-hydroxyl RNA [References 15, 16 and 25]. Moreover, RNAs having a 2' fluoro group have high affinity since the RNAs form very strong intramolecular helices, leading to thermodynamically stable and rigid tertiary structures [Reference 21].

As the result of SELEX, 2'-fluoro selected RNA aptamers were classified into two major groups, named #9 (SEQ ID NO. 1) and #24 (SEQ ID NO. 2), respectively. The two aptamer groups contained entirely different selected sequences. They were predicted to have stable secondary structures, as shown in FIG. 1, using the MULFOLD program [Reference 30].

The predicted structures also showed that the two aptamer groups have different configurations. Selected RNA #9 is comprised of one apical stem-loop. In contrast, selected RNA #24 has two apical stem-loop structures.

The sequences of both aptamers, selected from a random region of the RNA library, are present in these apical stem-loop part(s), suggesting the possibility that the apical stem-loop configuration might be involved in direct binding to the NS5B.

FIG. 1 shows sequences determined from 14 RNA aptamers selected after 8 rounds of in vitro selection. Two different RNA sequences were found in these clones, and #9 and #24 were present in 8 and 6 instances, respectively. In this figure, C and U correspond to 2'-fluoro C and 2'-fluoro U, respectively. The stable secondary RNA structure was determined using the MULFOLD program. Nucleotides 25 to 64 in the RNAs of SEQ ID NOS. 1 and 2 represent the sequences selected from a random region of the RNA library.

Example 2

Binding Specificity of RNA Aptamer

To evaluate binding specificity of the 2'-fluoro selected RNA aptamer, precipitation experiments were performed with the internally radiolabeled RNA aptamers selected in Example 1 (FIG. 2). Labeled and purified RNAs were incubated with proteins as described above, followed by the extraction of bound RNAs.

FIG. 2 shows the binding of 2'-fluoro selected RNA aptamers to HCV NS5B. One nM of internally radiolabeled original library RNA, RNA aptamer #9, or RNA aptamer #24 was incubated with (+E) or without (−E) NS5B (100 nM), and RNA-protein complexes were precipitated with Ni-NTA beads. Bound RNAs were extracted and analyzed on a 6% polyacrylamide gel with urea. Lane I contains 10% of each input-labeled RNA.

As is understood from the data of FIG. 2, the original library RNA with 2-fluoro pyrimidines bound to neither Ni-NTA bead nor the target HCV NS5B protein (lanes 1-3), whereas both selected RNA aptamers #9 and #24 were shown to bind to HCV NS5B (lanes 4-9). Notably, selected RNA aptamer #24 bound to the target protein more strongly than selected RNA aptamer #9. This may be because the selected RNA aptamer #24 binds to the HCV NS5B with higher affinity.

In addition, the selected RNA aptamers were not able to bind to other His-tagged HCV proteins such as NS3 helicase, thus excluding possible nonspecific binding to the histidine moieties of the NS5B protein, and, moreover, indicating the specific interaction of the aptamers with the target HCV NS5B.

Example 3

Binding Affinity of RNA Aptamer

To estimate the affinity of the selected RNA aptamer-HCV NS5B interaction, a gel retardation experiment was used with trace amounts of radiolabeled RNA aptamers and increasing amounts of the RNA-dependent RNA polymerase (FIG. 3). In this regard, the radiolabeled RNA aptamers were incubated with the target proteins for a gel shift analysis.

FIG. 3 shows the high binding affinity of the selected RNA aptamers to the HCV NS5B replicase. Internally radiolabeled RNA aptamer #9 (50 μM, FIG. 3A) or RNA aptamer #24 (50 μM, FIG. 3B) was incubated with an increasing amount of the HCV NS5B replicase (0-320 nM). The resulting NS5B-RNA complexes, C, were separated from the unbound free RNA, F, in a 4% nondenaturing acrylamide gel.

FIG. 3C is a graph in which the percentage of RNA bound to HCV NS5B was calculated by determining the fraction of radioactivity present in the RNA-HCV NS5B complexes. The values shown represent the means of three separate measurements.

As is understood from the data of FIG. 3, the original library RNA, containing 40-nt long random sequences, exhibited little affinity to the HCV NS5B even at the highest concentration of the protein. By contrast, both 2'-fluoro selected RNA aptamers #9 and #24 efficiently formed respective shifted nucleoprotein complexes with the HCV NS5B in dose-dependent manners, and exhibited high affinity with an apparent dissociation constant ($K_d$) of about 18 nM and 5 nM, respectively. Notably, selected RNA #24 was able to bind to the target protein 4 times better than was #9, indicating more efficient binding activity of the selected RNA #24.

Example 4

Inhibition of HCV Replication with RNA Aptamer

The selected RNA aptamers of the present invention, which were observed to specifically bind to the HCV NS5B at high affinity, were evaluated for their activity to suppress HCV replication in human liver cells using the recently developed HCV subgenomic replicon systems [References 12 and 17] (FIG. 4).

To determine whether the selected RNA aptamers inhibited the intracellular HCV replication, the level of synthesized HCV negative (−) strand RNA in hepatocarcinoma Huh-7 cells by RT-PCR was quantified 72 h after cotransfection with the HCV replicon RNA and various RNA competitors. The amount of HCV RNA in cells transfected with the HCV replicon alone was compared with that of HCV RNA in celled transfected with the HCV replicon, along with various RNA competitors. An electroporation experiment was employed to determine RNA transfection into Huh-7 cells, with the HCV replicon RNA along with tRNA, or with an RNA aptamer against an unrelated target protein, such as an autoantibody causing myasthenia gravis (MG RNA aptamer) [Reference 25], or with the selected RNA aptamer #9 or #24. After 72 hrs of transfection, total RNA was isolated and reverse-transcribed for the amplification of the (−) strand of HCV cDNA or of β-actin cDNA. Values were normalized to that of β-actin.

FIG. 4 is a graph showing the inhibition of the replication of the HCV replicon by 2'-fluoro selected RNA aptamers. Huh-7 cells were mock transfected, or were transfected with HCV subgenomic replicon RNA without any competitor RNAs (w/o RNA), or along with MG aptamer RNA, selected RNA aptamer #9, or RNA aptamer #24. An HCV (−) subgenomic RNA strand was amplified by RT-PCR. No cDNA was amplified by PCR without RT (w/o RT) from cells transfected with RNA aptamer #24. An amplified β-actin cDNA was loaded as an internal control. HCV RNA values were first normalized to β-actin RNA amounts, and the HCV RNA level was then expressed relative to the level in cells transfected with the HCV replicon RNA alone. The averages of measurements performed three separate times are shown.

As shown in FIG. 4, nonspecific RNA such as tRNA hardly affected the HCV subgenomic RNA synthesis. By contrast, RNA aptamer #9 and #24 to the HCV NS5B inhibited the RNA synthesis of the HCV replicon by up to 27% and 47%, respectively.

Unrelated 2'-fluoro MG RNA aptamer was not able to protect liver cells from the replication of HCV replicon RNA, which strongly indicates that the inhibition of HCV replication by the selected RNAs of the present invention is mainly due to the specific interaction of the selected RNA aptamers with the HCV NS5B, expressed by the HCV replicon in cells (FIGS. 2 and 3).

In accordance with the analysis of binding efficacy and affinity of the selected RNAs, the selected RNA aptamer #24 inhibited the RNA replication of the HCV replicon more efficiently than RNA aptamer #9 (FIG. 4). This implies that the bioactivity of RNA aptamers to prohibit HCV replication could be improved by enhancing the binding affinity of the aptamers to the target HCV proteins.

Example 5

Optimization of RNA Aptamer

Selected aptamers #9 and #24 are 89-nt and 92-nt in size, respectively, which are too long to chemically synthesize with ease. RNA aptamers are known to be easily chemically synthesized when they are 40-nt or smaller (Reference 26). In addition, because they may form various structural configurations, long RNA aptamers are generally not considered optimal.

An experiment was conducted for the optimization of the selected RNA aptamers by reducing their sizes. To this end, truncated forms of the selected RNA aptamers (#9 and #24) were constructed by in vitro transcription using T7 polymerase.

RNA aptamer #24 in smaller size was observed to have lower affinity, indicating that the full length (92 nt) form of the RNA aptamer #24 is ideal. In consideration of chemical synthesis, thus, RNA aptamer #24, although having excellent affinity to the target protein, is not preferable.

Three different truncated forms of RNA aptamer #9 were constructed (FIG. 5A).

RNA aptamer #9-t1 has a size of 45 nt, corresponding to nt 17-61 of the sequence of RNA aptamer #9, and is comprised of an apical loop-stem and a mid bulge-stem.

RNA aptamer #9-t2 has a size of 29 nt, corresponding to nt 25-53 of the sequence of RNA aptamer #9, and is comprised of an apical loop-stem.

RNA aptamer #9-t3 has a size of 23 nt corresponding to nt 28-50 of the sequence of RNA aptamer #9, and is comprised of a partial apical loop-stem.

These RNA aptamers were analyzed for binding affinity for HCV NS5B using the SPR technique (FIG. 5B). As seen, the library RNA showed a KD of as high as 933 nM, whereas the KD of #9-t3 was only 40.4 nM, implying that a partial sequence of the apical loop-stem cannot alone confer high binding affinity. In contrast, #9-t1 and #9-t2 were observed to bind well to NS5B at 8.4 nM and 2.6 nM KD, respectively.

Notably, RNA aptamer #942, which is comprised of an apical loop-stem only, was found to be optimal because it binds to HCV NS5B at higher affinity than does the full-length RNA aptamer #9, in addition to having a small size of 29 nt.

FIG. 5A shows stable secondary RNA structures, determined using the MULFOLD program (Reference 30). In this figure, C and U correspond to 2'-fluoro C and 2'-fluoro U, respectively. Nucleotides 25 to 64 in the RNAs represent the sequences selected from a random region of the RNA library. In FIG. 5B are summarized the KD values of RNA aptamers to HCV NS5B, measured through SPR analysis.

Example 6

Inhibition of HCV Replication with Optimized RNA Aptamer

An experiment similar to that illustrated in FIG. 4 was conducted to examine whether the optimized RNA aptamer #9-t2 of Example 5 effectively inhibits HCV replication. The optimized RNA aptamers of the present invention was evaluated for activity to suppress HCV replication in human liver cells using HCV subgenomic replicon systems [References 12 and 17] (FIG. 6). HCV replicon RNA and various RNA aptamers were transfected into hepatocarcinoma Huh-7 cells. After 72 hrs of transfection, total RNA was isolated and reverse-transcribed for the amplification of the (−) strand of HCV cDNA or for the amplification of β-actin cDNA. Values were normalized to that of β-actin.

FIG. 6 is a graph showing the inhibition of replication of HCV replicon by truncated forms of the RNA aptamer. Huh-7 cells were mock transfected, or were transfected with the HCV subgenomic replicon RNA without any competitor RNAs (w/o RNA), or along with RNA aptamer #9, or the truncated forms, RNA aptamer #9-t1, #9-t2 or #9-t3#24. The HCV (−) subgenomic RNA strand was amplified by RT-PCR. HCV (−) RNA values were first normalized to (β-actin RNA amounts, and the HCV RNA level was then expressed relative to the level in cells transfected with the HCV replicon RNA alone. Averages of measurements performed three separate times are shown.

As shown in FIG. 6, RNA aptamer #9 to the HCV NS5B showed the inhibition of RNA synthesis of the HCV replicon by up to 30%, as in FIG. 4. As for #9-t3, which lacks binding affinity for NS5B, it was found to inhibit the RNA synthesis of the HCV replicon by up to 15%. These data demonstrate that the loss of binding affinity leads to the loss of the ability to suppress HCV replication.

By contrast, #9-t1 showed the inhibition of RNA synthesis of the HCV replicon by up to 38%. Further, RNA aptamer #942, which is only 29 nt in size, showed inhibition as high as 53%. These data indicate that the truncated forms of RNA aptamer #9 can inhibit HCV replication more effectively than the full-length aptamer, and that the truncated RNA aptamers, having greater binding affinity for the target protein than the full-length RNA aptamer, are also improved in activity to suppress HCV replication.

Notably, the optimized RNA aptamer #9-t2 is very useful in the inhibition of HCV replication because it is small enough to be readily chemically synthesized, with a great improvement in binding affinity for HCV NS5B as well as in ability to suppress HCV replication.

Example 7

Inhibition of HCV Replication with Chemically Synthesized RNA Aptamer

The optimized RNA aptamer #9-t2 described above was chemically synthesized and evaluated for inhibition against HCV replication. The aptamer was tagged at 3' end with idT to protect it from exonuclease degradation. It was also modified at 5' end with a cholesteryl group so as to pass through cell membranes without the aid of any transfectant.

An expected structure of Chol-RM9 t2 (SEQ ID NO. 17), a chemically synthesized version of 2'-F RNA aptamer in accordance with the present invention, is shown in FIG. 7.

Also, the optimized RNA aptamer #9-t2 was chemically synthesized with a cholesteryl group and idT, tagged at the 5' end and the 3' end, respectively. 2'-F represents a pyrimidine nucleotide having 2'-fluoro instead of 2'-OH.

Sequences and structures of the chemically synthesized RNA aptamer (Chol-RM9 t2; SEQ ID NO. 17) and a mutant RNA aptamer (Chol-Mu-RM9 t2; different only in loop sequence from Chol-RM9 t2), incapable of binding to NS5B are shown in FIG. 8.

In order to examine whether Chol-RM9 t2 effectively inhibits HCV replication, an experiment was performed as illustrated in FIG. 9. In this regard, when the chemically synthesized RNA aptamers were reacted, in the absence of a transfectant, with an Huh-7 cell system, in which the HCV subgenomic replicon was stably replicated, they were measured for activity to suppress HCV replication.

After Huh-7 cells in which the HCV subgenomic replicon was stably replicated were treated with various concentrations of Chol-RM9 t2 or Chol-Mu-RM9 t2 for 48 hrs, total RNA was isolated and subjected to real-time RT-PCT for the amplification of the (−) strand of HCV cDNA or for the amplification of GAPDH cDNA. Values were normalized to that of GAPDH.

FIG. 9 is a graph showing the inhibition of replication of the HCV replicon by the chemically synthesized RNA aptamers. Huh-7 cells were mock transfected, or were treated with the chemically synthesized RNA aptamers. Thereafter, the HCV (−) subgenomic RNA strand was amplified by real-time PCR. HCV (−) RNA values were first normalized to GAPDH RNA amounts, and the HCV RNA level was then expressed relative to the level in cells mock transfected therewith. This experiment was conducted five times separately, and values are expressed as averages and standard deviations.

As shown in FIG. 9, no effects on HCV replication were detected when the cells were treated with high concentrations of the mutant RNA aptamer. In contrast, Chol-RM9 t2 was found to inhibit the RNA replication of the HCV subreplicon in a dose-dependent manner by up to 80%. Chol-RM9 t2 was observed to have an IC50 of about 2 mM against HCV replication.

As described above, the chemically synthesized RNA aptamer exhibiting permeability into cells in accordance with the present invention can effectively inhibit HCV replication, and this inhibition is based on the specific interaction of the RNA aptamer having a sequence specific for NS5B, but not on the non-specific reaction of the cholesteryl group attached to the RNA aptamer. Accordingly, the chemically synthesized Chol-RM9 t2 may be a potent candidate for drugs for use in the treatment of hepatitis C, because it can readily pass through HCV.

INDUSTRIAL APPLICABILITY

As described hitherto, nuclease-resistant RNA aptamers are provided for inhibiting the replication of HCV replicon. Also, the present invention provides a kit for the diagnosis of HCV infection using the RNA aptamers and an agent for inhibiting HCV. The RNA aptamers according to the present invention are resistant to nucleases and can function to suppress the activity of NS5B, an RNA-dependent RNA polymerase, which is a central catalytic enzyme HCV replication. The RNA aptamers show very low association constants at the nanomolar level for the target proteins (that is, they bind specifically to the target proteins with high affinity). Further, when introduced into human liver cells, the RNA aptamers of the present invention effectively inhibit RNA synthesis of the HCV replicon.

REFERENCE DOCUMENTS

1. Bae, S.-J., J.-H. Oum, S. Sharma, J. Park, and S.-W. Lee. 2002. In vitro selection of specific RNA inhibitors of NFATc. *Biochem. Biophys. Res. Commun.* 298: 486-492.
2. Behrens, S.-E., L. Tomei, and R. De Francesco. 1996. Identification and properties of the RNA-dependent RNA polymerase of the hepatitis C virus. *EMBO J.* 15: 12-22.
3. Biroccio, A., J. Hamm, I. Incitti, R. De Francesco, and L. Tomei. 2002. Selection of RNA aptamers that are specific and high-affinity ligands of the hepatitis C virus RNA-dependent RNA polymerase. *J. Virol.* 76: 3688-3696.
4. Burgstaller, P., A. Girod, and M. Blind. 2002. Aptamers as tools for target prioritization and lead identification. *Drug Discov. Today* 7: 1221-1228.
5. Cload, S. T., T. G. McCauley, A. D. Keefe, J. M. Healy, and C. Wilson. 2006. Properties of therapeutic aptamers, pp. 363-416. In S. Klussmann (ed.). The Aptamer Handbook, Wiley-VCH Verlag GmbH & Co. KGaA, Weinheim.
6. De Francesco, R. 1999. Molecular Virology of the hepatitis C virus. *J. Hepatol.* 312: 47-53.
7. Ellington, A. D. and J. W. Szostak. 1990. In vitro selection of RNA molecules that bind specific ligands. Nature 346: 818-822.
8. Gold, L., P. Allen, J. Binkley, D. Brown, D. Schneider, S. R. Eddy, C. Tuerk, L. Green, S. Macdougal, and D. Tasset. 1993. RNA: the shape of things to come, pp. 497-510. In: R. F. Gestelend and J. F. Atkins (eds.). The RNA World, Cold Spring Harbor Press, Cold Spring Harbor, N.Y.
9. Hwang, B., Han, K., and S. W. Lee. 2003. Prevention of passively transferred experimental autoimmune myasthenia gravis by an in vitro selected RNA aptamer. *FEBS Lett.* 548: 85-89.
10. Hwang, B., J. S. Cho, H. J. Yeo, J.-H. Kim, K. M. Chung, K. Han, S. K. Jang, and S.-W. Lee. 2004. Isolation of specific and high-affinity RNA aptamers against NS3 helicase domain of hepatitis C virus. RNA 10: 1277-1290.
11. Hwang, B. and S.-W. Lee. 2005. Analysis of in vivo interaction of HCV NS3 protein and specific RNA aptamer with yeast three-hybrid system. *Journal of Microbiology and Biotechnology* 15: 660-664.

12. Krieger, N., V. Lohmann, and R. Bartenschlager. 2001. Enhancement of hepatitis C virus RNA replication by cell culture-adaptive mutations. *J. Virol.* 75: 4614-4624.
13. Kumar, P. K., K. Machida, P. T. Urvil, N. Kakiuchi, D. Vishnuvardhan, K. Shimotohno, K. Taira, and S. Nishikawa. 1997. Isolation of RNA aptamers specific to the NS3 protein of hepatitis C virus from a pool of completely random RNA. *Virology* 237: 270-282.
14. Lauer, G. M. and B. D. Walker. 2001. Hepatitis C virus infection. *New Engl. J. Med.* 345: 41-52.
15. Lee, S. W. and B. Sullenger. 1996. Isolation of a nuclease resistant decoy RNA that selectively blocks autoantibody binding to insulin receptors on human lymphocytes. *J. Exp. Med.* 194: 315-324.
16. Lee, S. W. and B. Sullenger. 1997. Isolation of a nuclease-resistant decoy RNA that can protect human acetylcholine receptors from myasthenic antibodies. *Nature Biotechnol.* 15: 41-45.
17. Lohmann, V., F. Korner, J. Koch, U. Herian, L. Theilmann, and R. Bartenschlager. 1999. Replication of subgenomic hepatitis C virus RNAs in a hepatoma cell line. *Science* 285: 110-113.
18. Moradpour, D., V. Brass, R. Gosert, B. Wolk, and H. Blum. 2002. Hepatitis C: molecular virology and antiviral targets. *Trends Mol. Med.* 8: 476-482.
19. Ng, E. W. M., D. T. Shima, P. Calias, E. T. Cunningham, Jr., D. R. Guyer, and A. P. Adamis. 2006. Pegaptanib, a targeted anti-VEGF aptamer for ocular vascular disease. *Nature Rev. Drug Discov.* 5: 123-132.
20. Nishikawa, F., N. Kakiuchi, K. Funaji, K. Fukuda, S. Sekiya, and S. Nishikawa. 2003. Inhibition of HCV NS3 protease by RNA aptamers in cells. *Nucleic Acids Res.* 31: 1935-1943.
21. Pagratis, N. C., C. Bell, Y. F. Chang, S. Jennings, T. Fitzwater, D. Jellinek, and C. Dang. 1997. Potent 2'-amino, and 2'-fluoro-2' deoxyribonucleotide RNA inhibitors of keratinocyte growth factor. *Nature Biotechnol.* 15: 68-73.
22. Park, C.-H., Y.-H. Kee, J,-H. Lee, J.-H. Oh, J.-C. Park, and H.-J. Myung. 1999. Purification and characterization of recombinant hepatitis C virus replicase. *J. Microbiol. Biotechnol.* 9: 881-884.
23. Purcell, R. 1997. The hepatitis C virus: overview. *Hepatology* 26(Supple. 1): S11-S14.
24. Rusconi, C. P., J. D. Roberts, G. A. Pitoc, S. M. Nimjee, R. R. White, G. Jr. Quick, E. Scardino, W. P. Fay, and B. A. Sullenger. 2004. Antidote-mediated control of an anticoagulant aptamer in vivo. *Nature Biotechnol.* 22:1423-1428.
25. Seo, H. S. and S. W. Lee. 2000. In vitro selection of the 2'-fluoro-2'-deoxyribonucleotide decoy RNA inhibitor of myasthenic autoantibodies. *J. Microbiol. Biotechnol.* 10: 707-713.
26. Sullenger, B. A. and E. Gilboa. 2002. Emerging clinical applications of RNA. *Nature* 418: 252-258.
27. Thiel, K. 2004. Oligo oligarch—the surprisingly small world of aptamers. *Nat. Biotechnol.* 22:649-651.
28. Tuerk, C. and L. Gold. 1990. Systematic evolution of ligands by exponential enrichment: RNA ligands to bacteriophage T4 DNA polymerase. *Science* 249: 505-510.
29. Vo, N. V., J. W. Oh, and M. M. Lai. 2003. Identification of RNA ligands that bind hepatitis C virus polymerase selectively and inhibit its RNA synthesis from the natural viral RNA templates. *Virology* 307: 301-316.
30. Zuker, M. 2003. Mfold web server for nucleic acid folding and hybridization prediction. *Nucleic Acids Res.* 31: 3406-3415.

---

The invention claimed is:

1. A nuclease-resistant RNA aptamer, capable of binding specifically to hepatitis C virus (HCV) NS5B and inhibiting the proliferation of an HCV replicon, comprising at least one sequence selected from a group consisting of SEQ ID NOS. 1 to 4, in which a fluoro group is substituted for 2'-hydroxy of both U (uracil) and C (cytosine) bases, and SEQ ID NO. 17, in which a fluoro group is substituted for 2'-hydroxy of both U (uracil) and C (cytosine) bases, and which is tagged with a cholesteryl group at a 5' end and with idT at a 3' end.

2. A kit for diagnosis of HCV, comprising a container which contains at least one RNA aptamer, capable of binding specifically to hepatitis C virus (HCV) NS5B and inhibiting the proliferation of an HCV replicon, comprising at least one sequence selected from a group consisting of SEQ ID NOS. 1 to 4, in which a fluoro group is substituted for 2'-hydroxy of both U (uracil) and C (cytosine) bases, and SEQ ID NO. 17, in which a fluoro group is substituted for 2'-hydroxy of both U (uracil) and C (cytosine) bases, and which is tagged with a cholesteryl group at a 5' end and with idT at a 3' end.

3. An inhibitor of hepatitis C virus, capable of binding specifically to hepatitis C virus (HCV) NS5B and inhibiting proliferation of an HCV replicon, comprising at least one RNA aptamer, capable of binding specifically to hepatitis C virus (HCV) NS5B and inhibiting the proliferation of an HCV replicon, comprising at least one sequence selected from a group consisting of SEQ ID NOS. 1 to 4, in which a fluoro group is substituted for 2'-hydroxy of both U (uracil) and C (cytosine) bases, and SEQ ID NO. 17, in which a fluoro group is substituted for 2'-hydroxy of both U (uracil) and C (cytosine) bases, and which is tagged with a cholesteryl group at a 5' end and with idT at a 3' end.

\* \* \* \* \*